(12) United States Patent
Shanmugam et al.

(10) Patent No.: US 11,628,143 B1
(45) Date of Patent: Apr. 18, 2023

(54) TABLET FOR ORAL SUSPENSION

(71) Applicant: Novitium Pharma LLC, East Windsor, NJ (US)

(72) Inventors: Muthusamy Shanmugam, Delray Beach, FL (US); Shivanand Premanand Puthli, Dayton, NJ (US)

(73) Assignee: Novitium Pharma LLC, East Windsor, NJ (US)

( * ) Notice: Subject to any disclaimer, the term of this patent is extended or adjusted under 35 U.S.C. 154(b) by 0 days.

(21) Appl. No.: 17/840,382

(22) Filed: Jun. 14, 2022

(51) Int. Cl.
*A61K 9/20* (2006.01)
*A61K 31/17* (2006.01)
*A61K 9/00* (2006.01)

(52) U.S. Cl.
CPC .......... *A61K 9/2054* (2013.01); *A61K 9/0095* (2013.01); *A61K 9/2009* (2013.01); *A61K 9/2013* (2013.01); *A61K 9/2027* (2013.01); *A61K 31/17* (2013.01)

(58) Field of Classification Search
CPC ........ A61K 9/002; A61K 9/0012; A61K 9/10; A61K 9/20; A61K 9/2004; A61K 9/2072; A61K 9/2095
See application file for complete search history.

(56) References Cited

U.S. PATENT DOCUMENTS

2020/0368192 A1* 11/2020 Barchielli ............ A61K 31/197

FOREIGN PATENT DOCUMENTS

| CN | 105056246 A | 11/2015 | |
|---|---|---|---|
| EP | 2777696 A1 * | 9/2014 | ........... A61K 31/194 |
| EP | 2 777 696 B1 | 4/2021 | |
| WO | 2018/095848 A1 | 5/2018 | |
| WO | WO-2019158509 A1 * | 8/2019 | ............. A61K 47/02 |
| WO | 2020/239882 A1 | 12/2020 | |
| WO | WO-2020239882 A1 * | 12/2020 | ........... A61K 31/133 |

OTHER PUBLICATIONS

ASTM E-11-20, available online at newarkwire.com/pdf/ASTM%20E11-20.pdf, last accessed on Apr. 14, 2022 ("ASTM E-11").
Carbaglu® Prescribing Information, as of Aug. 5, 2021.
CAS Registry No. 1188-38-1, carglumic acid (2022).
CAS Registry No. 98-79-3, Impurity 1 (2022).
CAS Registry No. 17027-50-8, Impurity 2 (2022).
CAS Registry No. 2380660-24-0 (2022).
European Medicines Agency Scientific Discussion related to Carbaglu® (2004).
Primellose® (croscarmellose sodium) safety information (2020).
Product Bulletin for Stepanol® WA-100 NF/USP (2015).
Product information for CAB-O-SIL® (2021).
Product Information for Ligamed MF-2-K (2018).
Product Information for Pruv®, accessible at www.jrspharma.com/pharma-wAssets/docs/brochures/pruv-gb-1809.pdf, last accessed on Apr. 14, 2022.
Product Specifications for Avicel® PH-113 (2003).
Product Specifications for Pearlitol® 200 SD (2020).
Remington: Practice of the science and pharmacy, vol. II, pp. 1598-1649 (1995).
Technical information for Kollidon® (2019).
The FDA's Jun. 2020 Draft Guidance on Carglumic Acid, available at www.accessdata.fda.gov/drugsatfda_docs/psg/PSG_022562.pdf, last accessed on Apr. 14, 2022.
The FDA's Oct. 13, 2021 approval letter with respect to ANDA 213729 held by Novitum Pharma LLC.
The United States Pharmacopeia 35—National Formulary 30 (2012), pp. 3-15, 258-265, 293-295, 317-318, 336-339, 343-344, 867-870, 5637-5640, 5642-5649 ("USP 35").

* cited by examiner

*Primary Examiner* — Micah Paul Young
(74) *Attorney, Agent, or Firm* — Merchant & Gould P.C.; Daniel R. Evans

(57) ABSTRACT

Disclosed herein is a tablet for oral suspension comprising carglumic acid and its use.

19 Claims, No Drawings

TABLET FOR ORAL SUSPENSION

FIELD

Disclosed herein is a tablet for oral suspension comprising carglumic acid and its use.

BACKGROUND

N-acetyl-glutamate synthase (NAGS) is an enzyme that catalyzes the reaction of glutamic acid and acetyl-CoA to form N-acetyl-glutamate.

NAGS deficiency is a very rare inborn error of metabolism. NAGS deficiency, which is the rarest congenital urea cycle disorder, results in a severe defect of ammonia detoxification with a rapid lethal course in most cases. The estimated prevalence of NAGS deficiency is 0.00125 per 10,000 persons.

Ammonia is eliminated by means of the so-called urea cycle, where ammonia is converted to urea using several enzymatic processes. The first committed step of the urea cycle is the formation of carbamoyl phosphate from the reaction of ammonia and carbon dioxide catalyzed by carbamoyl-phosphate synthase (CPS), where NAG serves as the essential allosteric activator of CPS. Thus, NAGS deficiency results in reduced levels of NAG, limited activation of CPS, and limited elimination of ammonia, which results in elevated levels of ammonia, referred to as hyperammonaemia. NAGS deficiency leads to various neurological and gastrointestinal (including hepatic) symptoms and the NAGS deficiency severity depends on the degree of enzymatic deficiency.

Carglumic acid ("CGA") mimics the action of NAG and activates CPS, which permits production of carbamoyl phosphate, thereby restoring the function of the urea cycle. Carbaglu® (carglumic acid) tablets for oral suspension was approved by the U.S. Food and Drug Administration ("FDA") on Mar. 18, 2010. Carbaglu® is indicated generally for the treatment of hyperammonaemia in pediatric and adult patients having NAGS deficiency. Carbaglu® (carglumic acid) tablets for oral suspension contains 200 mg of carglumic acid with the following inactive ingredients: croscarmellose sodium, hypromellose, microcrystalline cellulose, silica colloidal anhydrous, sodium lauryl sulfate, and sodium stearyl fumarate. See Carbaglu® Prescribing Information at Sect. 11; see also Mattei at para. 62. Carbaglu® (carglumic acid) tablets for oral suspension dispersed in water prior to administration.

The Carbaglu® prescribing information states that Carbaglu® should be stored in the original, unopened, container under refrigerated conditions (viz., 2° C. to 8° C.). The Carbaglu® prescribing information states that any unused Carbaglu® tablets should be discarded after one month once the bottle is opened and stored at room temperature.

Carbaglu® is associated with numerous disadvantages, which include the requirement to store at refrigerated temperatures, as well as the limited in use storage time (viz., one-month). Additional advantages relate to a considerable amount of microcrystalline cellulose, which do not solubilize well in water, and thus, create a high volume of sediment at the bottom of the dispersing container, as well as a discomfort to the patient during swallowing of the gritty/sandy excipient. Additionally, a partial dispersion of non-solubilized carglumic acid when high dosages are administered through a limited amount of water (limitation due to the intrinsic solubility of the carglumic acid at its natural pH). Further, improperly suspended product (and the presence of insoluble residues) generates a risk that devices (e.g., nasogastric tubing) become clogged during patient use during intubation.

Others have endeavored to produce carglumic acid tablets but have failed to achieve a tablet product deemed to be therapeutically equivalent to Carbaglu®. See Xingfa and Kawale.

SUMMARY

Disclosed herein is a tablet for oral suspension comprising carglumic acid and its use.

DETAILED DESCRIPTION

The following paragraphs detail various embodiments of the table for oral suspension.

Tablets for Oral Suspension

A first embodiment disclosed herein relates to a tablet for oral suspension, comprising: carglumic acid in an amount of about 200 mg; a diluent comprising microcrystalline cellulose, mannitol, or a combination thereof in an amount of from 228 mg to 280 mg; a suspending agent comprising a povidone in an amount of from 4.4 mg to about 5.4 mg; a disintegrant comprising sodium croscarmellose in an amount of from 17 mg to 21 mg; a wetting agent comprising sodium stearyl fumarate, magnesium stearate, sodium lauryl sulfate, or a combination thereof in an amount of from 6.35 mg to 7.65 mg; and a glidant comprising colloidal silicon dioxide in an amount of from 2.3 mg to 2.8 mg.

One will appreciate that povidone is available commercially (e.g., Kollidon®) with different grades that relate generally to the weight average molecular weight (Mw). For example, Kollidon® 25 has a Mw of from 28,000 Daltons (Da) to 34,000 Da, Kollidon® 30 has a Mw of from 44,000 Da to 54,000 Da, while Kollidon® 90 has a Mw of from 900,000 Da to 1,200,000 Da.

In one aspect of the first embodiment, the tablet for oral suspension comprises povidone having a weight average molecular weight of from 44 kDa to 54 kDa.

In another aspect of the first embodiment, the tablet for oral suspension comprises a diluent comprising microcrystalline cellulose in an amount of from 149 mg to 183 mg and mannitol in an amount of from 79 mg to 98 mg.

In yet another aspect of the first embodiment, the tablet for oral suspension comprises a wetting agent comprising sodium stearyl fumarate in an amount of from 4.5 mg to 5.5 mg, magnesium stearate in an amount of from 1.4 mg to 1.6 mg, and sodium lauryl sulfate in an amount of from 0.45 mg to 0.55 mg.

A second embodiment disclosed herein relates to a tablet for oral suspension, comprising: carglumic acid in an amount of about 200 mg; a diluent comprising microcrystalline cellulose, mannitol, or a combination thereof in an amount of from 240 mg to 266 mg; a suspending agent comprising povidone having a weight average molecular weight of from 44 kDa to 54 kDa in an amount of from 4.6 to 5.1 mg; a disintegrant comprising sodium croscarmellose in an amount of from 18 mg to 20 mg; the wetting agent comprising sodium stearyl fumarate, magnesium stearate, sodium lauryl sulfate, or a combination thereof in an amount of from 6.7 mg to 7.4 mg; and a glidant comprising colloidal silicon dioxide in an amount of from 2.4 mg to 2.6 mg.

In an aspect of the second embodiment, the diluent comprises microcrystalline cellulose in an amount of from 158 mg to 174 mg and mannitol in an amount of from 82 mg to 92 mg.

In yet another aspect of the second embodiment, the wetting agent comprises sodium stearyl fumarate in an amount of from 4.8 mg to 5.3 mg, magnesium stearate in an amount of from 1.4 mg to 1.6 mg, and sodium lauryl sulfate in an amount of 0.5 mg.

A third embodiment disclosed herein relates to a tablet for oral suspension, comprising: carglumic acid in an amount of about 200 mg; a diluent comprising microcrystalline cellulose, mannitol, or a combination thereof in an amount of from 249 mg to 258 mg; a suspending agent comprising povidone having a weight average molecular weight of from 44 kDa to 54 kDa in an amount of from 4.8 to 5.0 mg; a disintegrant comprising sodium croscarmellose in an amount of from 18.6 mg to 19.4 mg; a wetting agent comprising sodium stearyl fumarate, magnesium stearate, sodium lauryl sulfate, or a combination thereof in an amount of from 6.87 mg to 7.13 mg; and a glidant comprising colloidal silicon dioxide in an amount of from 2.45 mg to 2.55 mg.

In an aspect of the third embodiment, the diluent comprises microcrystalline cellulose in an amount of from 163 mg to 169 mg and mannitol in an amount of from 86 mg to 89 mg.

In another aspect of the third embodiment, the wetting agent comprises sodium stearyl fumarate in an amount of from 4.9 mg to 5.1 mg, magnesium stearate in an amount of from 1.47 mg to 1.53 mg, and sodium lauryl sulfate in an amount 0.5 mg.

A fourth embodiment disclosed herein relates to a tablet for oral suspension, comprising: carglumic acid in an amount of about 200 mg; a diluent comprising microcrystalline cellulose, mannitol, or a combination thereof in an amount of 253.6 mg; a suspending agent comprising povidone having a weight average molecular weight of from 44 kDa to 54 kDa in an amount of 1.01 mg; a disintegrant comprising sodium croscarmellose in an amount of 19.0 mg; a wetting agent comprising sodium stearyl fumarate, magnesium stearate, sodium lauryl sulfate, or a combination thereof in an amount of 7 mg; and a glidant comprising colloidal silicon dioxide in an amount of 2.5 mg.

In an aspect of the fourth embodiment, the diluent comprises microcrystalline cellulose in an amount of 166 mg and mannitol in an amount of from 87.6 mg.

In another aspect of the fourth embodiment, the wetting agent comprises sodium stearyl fumarate in an amount of 5.0 mg, magnesium stearate in an amount of 1.5 mg, and sodium lauryl sulfate in an amount of 0.5 mg.

The following table summarizes additional embodiments contemplated herein along with the ingredients, their function, and the amount of ingredients (in mg).

In an aspect of any one of embodiments related to a tablet for oral suspension, the tablet comprises three equidistant lines for splitting the tablet into four equal portions each portion having a mass of about 122 mg.

Based on development studies, it was discovered that a lower compression force may provide a tablet with a low hardness and a high friability, while a higher compression force may provide a tablet that does not disintegrate within the specified time period. Accordingly, the tablet composition disclosed herein has a tablet hardness of from 6 kp to 14 kp, including all values in between, such as, for example, 8 kp, 10 kp, and 12 kp. As a point of reference, kp corresponds to kilopond, where 1 kilopond corresponds to 9.80665 Newtons. In one aspect, the tablet of any one the embodiments disclosed herein have a tablet hardness of about 10 kp.

An alternative embodiment relates to a capped bottle comprising one or more tablets of an embodiment disclosed herein and a desiccant, wherein the one or more tablets has a carglumic acid content of from 95.0% to 105% for two-years when the bottle is stored at 25° C.±2° C. and 60% relative humidity.

In one aspect of the alternative embodiment, the one or more tablets exhibits an in-use stability for 90-days or more (e.g., 120-days) when stored in the bottle at a temperature of from about 25° C. to about 30° C., where the bottle may be opened and closed daily.

As stated below, tablets for oral suspension may be suspended in a suitable medium, e.g., water, in an amount of about 2.5 mL. Thus, one aspect relates to an oral suspension comprising the tablet of an embodiment disclosed herein in whole or in part and about 2.5 mL of water. As stated herein, the tablet comprises three equidistant lines for splitting the tablet into four equal portions each portion having a mass of about 122 mg. Thus, the oral suspension may comprise an amount of carglumic acid of 50 mg, 100 mg, 150 mg, 200 mg, or more depending on number of split tablets or whole tablets dispersed in the water. In one aspect, the oral suspension exhibits a D(0.9) particle size of about 146 μm.

In view of the information disclosed herein, one may appreciate that the expression comprising may be replaced by the expression consisting of without departing from the fundamental meaning of the embodiments disclosed herein. In that regard, one will appreciate that the tablet embodiments disclosed herein do not include a basic agent (e.g., tromethamine) or an effervescent agent (e.g., an alkali/alkaline earth (bi)carbonate). In view of this consideration, one may consider several alternative embodiments, as stated below.

A first alternative embodiment disclosed herein relates to a tablet for oral suspension, consisting of: carglumic acid in

| Ingredients | Function | Amount (mg) | | | |
|---|---|---|---|---|---|
| Carglumic acid | API | 180-220 | 190-210 | 196-204 | 200.00 |
| Microcrystalline cellulose (MCC) | Diluent | 149-183 | 158-174 | 163-169 | 166.0 |
| Mannitol | | 79-98 | 82-92 | 86-89 | 87.60 |
| MCC + Mannitol | | 228-280 | 240-266 | 249-258 | 253.6 |
| Povidone | Suspending agent | 4.4-5.4 | 4.6-5.1 | 4.80-5.00 | 4.90 |
| Sodium croscarmellose | Disintegrant | 17-21 | 18-20 | 18.6-19.4 | 19.00 |
| Sodium stearyl fumarate (SSF) | Wetting agent | 4.5-5.5 | 4.8-5.3 | 4.9-5.1 | 5.00 |
| Magnesium stearate (MS) | | 1.4-1.6 | 1.43-1.58 | 1.47-1.53 | 1.50 |
| Sodium lauryl sulfate (SLS) | | 0.45-0.55 | 0.475-0.525 | 0.49-0.51 | 0.5 |
| SSF + MS + SLS | | 6.35-7.65 | 6.7-7.4 | 6.9-7.1 | 7.00 |
| Coll. Silicon dioxide | Glidant | 2.3-2.8 | 2.4-2.6 | 2.45-2.55 | 2.50 | an amount of about 200 mg; a diluent comprising microcrystalline cellulose, mannitol, or a combination thereof in an amount of from 228 mg to 280 mg; a suspending agent comprising a povidone in an amount of from 4.4 mg to about 5.4 mg; a disintegrant comprising sodium croscarmellose in an amount of from 17 mg to 21 mg; a wetting agent comprising sodium stearyl fumarate, magnesium stearate, sodium lauryl sulfate, or a combination thereof in an amount of from 6.35 mg to 7.65 mg; and a glidant comprising colloidal silicon dioxide in an amount of from 2.3 mg to 2.8 mg.

A second alternative embodiment disclosed herein relates to a tablet for oral suspension, consisting of: carglumic acid in an amount of about 200 mg; a diluent comprising microcrystalline cellulose, mannitol, or a combination thereof in an amount of from 240 mg to 266 mg; a suspending agent comprising povidone having a weight average molecular weight of from 44 kDa to 54 kDa in an amount of from 4.6 to 5.1 mg; a disintegrant comprising sodium croscarmellose in an amount of from 18 mg to 20 mg; the wetting agent comprising sodium stearyl fumarate, magnesium stearate, sodium lauryl sulfate, or a combination thereof in an amount of from 6.7 mg to 7.4 mg; and a glidant comprising colloidal silicon dioxide in an amount of from 2.4 mg to 2.6 mg.

A third alternative embodiment disclosed herein relates to a tablet for oral suspension, consisting of: carglumic acid in an amount of about 200 mg; a diluent comprising microcrystalline cellulose, mannitol, or a combination thereof in an amount of from 249 mg to 258 mg; a suspending agent comprising povidone having a weight average molecular weight of from 44 kDa to 54 kDa in an amount of from 4.8 to 5.0 mg; a disintegrant comprising sodium croscarmellose in an amount of from 18.6 mg to 19.4 mg; a wetting agent comprising sodium stearyl fumarate, magnesium stearate, sodium lauryl sulfate, or a combination thereof in an amount of from 6.87 mg to 7.13 mg; and a glidant comprising colloidal silicon dioxide in an amount of from 2.45 mg to 2.55 mg.

A fourth alternative embodiment disclosed herein relates to a tablet for oral suspension, consisting of: carglumic acid in an amount of about 200 mg; a diluent comprising microcrystalline cellulose, mannitol, or a combination thereof in an amount of 253.6 mg; a suspending agent comprising povidone having a weight average molecular weight of from 44 kDa to 54 kDa in an amount of 1.01 mg; a disintegrant comprising sodium croscarmellose in an amount of 19.0 mg; a wetting agent comprising sodium stearyl fumarate, magnesium stearate, sodium lauryl sulfate, or a combination thereof in an amount of 7 mg; and a glidant comprising colloidal silicon dioxide in an amount of 2.5 mg.

Tablet Manufacture

As explained in greater detail herein, tablets for oral suspension disclosed herein may be manufactured by sieving, mixing, and compressing. See, e.g., Remington at 1604-1605, 1610-1611, 1626-1627.

Prior to compression, the blend used for compression has a bulk density of about 0.57 g/mL, a tapped density of about 0.77 g/mL, a loss on drying of about 0.78% (0.78±0.07%), and carglumic acid (CGA) content of about 100%. Also prior to compression, the blend used for compression has a particle size distribution where about 64% of the material has a particle size of less than about 106 µm and about 36% of the material has a particle size greater than or equal to about 106 µm.

Methods of Use

Tablets disclosed herein may be used in a patient for the treatment of hyperammonemia due to NAGS deficiency, as explained in the prescribing information for Carbaglu® and/or the package insert for Abbreviated New Drug Application ("ANDA") 213729.

That said, an embodiment disclosed herein relates to a method for the treatment of acute hyperammonemia due to NAGS deficiency by administering to a patient in need thereof a therapeutically effective amount of carglumic acid. In one aspect, the patient is a pediatric patent. In yet another aspect, the patient is an adult patient.

Another embodiment disclosed herein relates to a method for the treatment of chronic hyperammonemia due to NAGS deficiency by administering to a patient in need thereof a therapeutically effective amount of carglumic acid. In one aspect, the patient is a pediatric patent. In yet another aspect, the patient is an adult patient.

As stated herein, tablets disclosed herein are dispersed in water (e.g., 2.5 mL) to obtain an oral suspension.

That said, one aspect relates to a method of treating acute hyperammonaemia, which comprises administering to a patient in need thereof a therapeutically effective amount of an oral suspension disclosed herein.

Yet another aspect related to a method of treating chronic hyperammonaemia, which comprises administering to a patient in need thereof a therapeutically effective amount of an oral suspension disclosed herein.

Another aspect relates to a method of treating either acute hyperammonaemia or chronic hyperammonaemia, which comprises administering to a patient in need thereof a therapeutically effective amount of an oral suspension disclosed herein, wherein the patient has at least one of the following pharmacokinetic parameters (i) a $C_{max}$ of from about 2,400 ng/mL to about 5,300 ng/mL, (ii) an $AUC_{0-\infty}$ of from about 23,000 hr*ng/mL to about 50,000 hr*ng/mL, and (iii) a $T_{max}$ of from about 1.5 hr to about 4 hr.

The respective $C_{max}$, $AUC_{0-\infty}$, and $T_{max}$ values include all values in between. For instance, the $C_{max}$ of from about 2,400 ng/mL to about 5,300 ng/mL includes, for example, about 2,500 ng/mL, about 2,700 ng/mL, about 2,900 ng/mL, about 3,100 ng/mL, about 3,300 ng/mL, about 3,500 ng/mL, about 3,700 ng/mL, about 3,900 ng/mL, about 4,100 ng/mL, about 4,300 ng/mL, about 4,500 ng/mL, about 4,700 ng/mL, about 4,900 ng/mL, and about 5,100 ng/mL. Further, the $AUC_{0-\infty}$ of from about 23,000 hr*ng/mL to about 50,000 hr*ng/mL include, for example, about 25,000 hr*ng/mL, about 27,000 hr*ng/mL, about 29,000 hr*ng/mL, about 31,000 hr*ng/mL, about 33,000 hr*ng/mL, about 35,000 hr*ng/mL, about 37,000 hr*ng/mL, about 39,000 hr*ng/mL, about 41,000 hr*ng/mL, about 43,000 hr*ng/mL, about 45,000 hr*ng/mL, about 47,000 hr*ng/mL, and about 49,000 hr*ng/mL. Additionally, the $T_{max}$ of from about 1.5 hr to about 4 hr includes, for example, about 2.0 hr, about 2.5 hr, about 3.0 hr, and about 3.5 hr.

Information that follows provides additional details concerning preparation of the oral suspension from the tablets.

Dosage for Acute Hyperammonemia Due to NAGS Deficiency

The recommended daily dosage of carglumic acid tablets for oral suspension in pediatric and adult patients for acute hyperammonemia due to NAGS deficiency is 100 mg/kg to 250 mg/kg. Thus, for a 60 kg patient, the carglumic acid daily dose ranges from about 6 g to about 15 g. Divide the daily dosage into 2 to 4 doses and round to the nearest 100 mg (i.e., half of a carglumic acid tablet for oral suspension). During acute hyperammonemic episodes, administer carglumic acid tablets for oral suspension with other ammonia lowering therapies, such as alternate pathway medications, hemodialysis, and protein restriction.

Dosage for Chronic Hyperammonemia Due to NAGS Deficiency

The recommended daily dosage of the tablets for oral suspension in pediatric and adult patients for chronic hyperammonemia due to NAGS deficiency is 10 mg/kg to 100 mg/kg. Divide the daily dosage into 2 to 4 doses and round to the nearest 100 mg (i.e., half of a Carglumic acid tablet for oral suspension). During maintenance therapy, the concomitant use of other ammonia lowering therapies and protein restriction may be needed based on plasma ammonia levels.

Therapeutic Monitoring

Closely monitor plasma ammonia levels. Titrate the tablets for oral suspension, disclosed herein, dosage to maintain the plasma ammonia level within the normal range for the patient's age, taking into consideration their clinical condition (e.g., nutritional requirements, protein intake, growth parameters, etc.). Adjust the recommended dosage in patients with moderate or severe renal impairment.

Dosage Adjustment in Patients with Renal Impairment

No dosage adjustment is warranted in patients with mild renal impairment (eGFR 60-89 mL/min/1.73 $m^2$). The recommended dosage of the tablet for oral suspension, disclosed herein, in patients with moderate or severe renal impairment is shown below.

Acute hyperammonemia due to NAGS deficiency with moderate renal impairment (eGFR 30-59 mL/min/1.73 $m^2$) administer 50 mg/kg/day to 125 mg/kg/day divided into 2 to 4 doses and rounded to the nearest 50 mg (i.e., one-quarter of a tablet for oral suspension).

Acute hyperammonemia due to NAGS deficiency with severe renal impairment (eGFR≤29 mL/min/1.3 $m^2$) administer 15 mg/kg/day to 60 mg/kg/day divided into 2 to 4 doses and rounded to the nearest 50 mg (i.e., one-quarter of a tablet for oral suspension).

Chronic Hyperammonemia due to NAGS deficiency with moderate renal impairment (eGFR 30-59 mL/min/1.73 $m^2$) administer 5 mg/kg/day to 50 mg/kg/day divided into 2 to 4 doses and rounded to the nearest 50 mg (i.e., one-quarter of a tablet for oral suspension).

Chronic Hyperammonemia due to NAGS deficiency with severe renal impairment (eGFR≤29 mL/min/1.3 $m^2$) administer 2 mg/kg/day to 25 mg/kg/day divided into 2 to 4 doses and rounded to the nearest 50 mg (i.e., one-quarter of a tablet for oral suspension).

Preparation and Administration

Disperse tablets for oral suspension in water. Do not swallow whole or crushed. Tablets for oral suspension do not dissolve completely in water, and undissolved particles of the tablet may remain in the mixing container. Take tablets for oral suspension immediately before meals or feedings. The tablet suspension has a slightly acidic taste. For all preparations, use in foods or liquids other than water has not been studied and is not recommended.

Oral Administration

For oral administration, administer tablets for oral suspension as follows. Add a minimum of 2.5 mL of water into a small cup for each tablet for oral suspension or each ½ or ¼ tablet for oral suspension needed for the prescribed dose. Add the tablet(s) for oral suspension to the water in the cup. Carefully stir the tablet(s) and water mixture. Swallow the mixture immediately. Pieces of the tablet(s) may remain in the cup. Rinse the cup with additional water and swallow the mixture immediately. Repeat as needed until no pieces of the tablet are left in the cup.

Use of an Oral Syringe for Oral Administration

For administration via an oral syringe, administer tablets for oral suspension as follows. Add a minimum of 2.5 mL of water into a small cup for each tablet for oral suspension or each ½ or ¼ tablet for oral suspension needed for the prescribed dose. Add the tablet(s) for oral suspension to the water in the cup. Carefully stir the tablet(s) and water mixture. Draw up the mixture in an oral syringe and administer immediately. Pieces of the tablet(s) may remain in the oral syringe. Refill the oral syringe with a minimum volume of water (1 mL to 2 mL) and administer immediately. Flush the oral syringe again, as needed, until no pieces of the tablet are left in the syringe.

Use of Nasogastric Tube (NG Tube) or Gastrostomy Tube (G-Tube) for Feeding Tube Administration For patients who have a NG tube or G-tube in place, administer tablets for oral suspension as follows. Add a minimum of 2.5 mL of water into a small cup for each tablet for oral suspension or each ½ or ¼ tablet for oral suspension needed for the prescribed dose. Add the tablet(s) for oral suspension to the water in the cup. Carefully stir the tablet(s) and water mixture. Draw up the mixture into a catheter-tip syringe. Administer the mixture immediately through the NG tube or G-tube. Pieces of the tablet(s) may remain in the catheter-tip syringe or the feeding tube. Flush immediately with 1 to 2 mL of additional water to clear the NG tube or G-tube. Flush the NG tube or G-tube again, as needed, until no pieces of the tablet are left in the syringe or the feeding tube.

The following examples serve to illustrate aspects of the tablets for oral suspension disclosed herein.

EXAMPLES

Unless stated otherwise, properties reported herein were measured consistent with general notices reported in USP 35, including, for example, bulk and tapped density <616>, HPLC<621>, disintegration <701>, dissolution <711>, loss on drying <731>, particle size distribution <786>, pH<791>, tablet friability <1216>, tablet strength <1217>.

Compositional Details

Compositional aspects of the tablets for oral suspension are disclosed herein. A representative composition of tablets for oral suspension (batch suitable for 75,000 tablets) is shown in Table 1.

TABLE 1

Compositional makeup of tablets for oral suspension

| Ingredients | Amount (mg/tablet) |
|---|---|
| Carglumic acid | 200.00 |
| Microcrystalline cellulose (Avicel PH-113) | 166.00 |
| Mannitol (Pearlitol SD 200) | 87.60 |
| Povidone (Kollidon K30) | 4.90 |
| Croscarmellose sodium (Primellose) | 19.00 |
| Sodium stearyl fumarate (Pruv) | 5.00 |
| Magnesium stearate (Ligamed MF-2-K) | 1.50 |
| Colloidal silicon dioxide (Cab-O-Sil M5P) | 2.50 |
| Sodium lauryl sulfate (Stepanol WA 100/NF/USP) | 0.50 |
| Total Tablet Mass (mg) | 487.00 |

A tablet batch size (75,000 tablets) was manufactured generally by the following method.

Pass carglumic acid through a Fitz Mill fitted with 1512-0020 stainless steel screen at high speed (4600±46 rpm) and knife forward condition. The milled CGA was passed through #20 stainless steel screen and each of the identified inactive ingredients was then passed through the specified (#20 or #40) stainless steel screen and loaded into 5 cu ft V-blender (inactive ingredients: a wetting agent (e.g., sodium lauryl sulfate (#20), magnesium stearate (#20), sodium stearyl fumarate (#40)), a glidant (e.g., colloidal silicon dioxide (#20)), a diluent (e.g., mannitol (#20) and microcrystalline cellulose (#20)), a suspending agent (e.g., povidone (#20)), a disintegrant (e.g., croscarmellose sodium (#20))). The components were blended at 25±1 rpm for about 5 min. to about 20 min.

Composition Properties

Ten samples of the blended mixture from step 6 ("Final Blend") were collected from ten (10) locations in the V-blender to evaluate numerous parameters, including, for example carglumic acid ("CGA") content, particle size distribution, bulk density, tapped density, and loss on drying using a moisture analyzer at 105° C. for 3-minutes. The blended mixture was in a double polyethylene bag lined container and the stored. Table 2 presents selected observable for the Final Blend of three separate batches.

TABLE 2

Selected Observables for Final Blends

| Observable | Batch 1 | Batch 2 | Batch 3 |
|---|---|---|---|
| Description | White to off-white powder | | |
| Bulk Density (g/mL) | 0.58 | 0.59 | 0.55 |
| Tapped Density (g/mL) | 0.78 | 0.76 | 0.76 |
| Loss on drying (%) | 0.76 | 0.73 | 0.86 |
| CGA Content (%)[a] | 99.4 (1.1) | 99.3 (0.6) | 100.0 (0.4) |
| Particle Size Distribution | | | |
| Sieve # (PS, μm) | % Retained | | |
| 20 (850) | 0.031 | 0.070 | 0.041 |
| 40 (425) | 0.304 | 0.157 | 0.105 |
| 60 (250) | 2.535 | 2.232 | 1.757 |
| 80 (180) | 6.967 | 6.870 | 7.160 |
| 100 (150) | 7.773 | 8.083 | 8.295 |
| 140 (106) | 17.624 | 17.957 | 17.811 |
| Pan (<106) | 64.608 | 64.288 | 64.641 |

[a]% CGA content represents the average of ten (10) samples collected from the ten (10) locations in the V-blender, including parenthetically % RSD.

Based on the analyzed results of Final Blends, one may see that the bulk density is about 0.57 g/mL (0.57±0.02 g/mL), the tapped density is about 0.77 g/mL (0.77±0.01 g/mL), the loss on drying is about 0.78% (0.78±0.07%), and the CGA content is about 99.6% (99.6±0.4%).

The analyzed results also show that the Final Blends have a particle size distribution where about 64% of the material has a particle size of less than about 106 μm and about 36% of the material has a particle size greater than or equal to about 106 μm.

Tablets for oral suspension were prepared by compression of the Final Blend using a die (0.2362×0.7087 inches), an upper punch (0.2362×0.7087 inches with 3 break lines), and a lower punch (0.2362×0.7087 inches with 3 break lines) operating at about 30 rpm (20-40 rpm), applying a compression strength of about 10 kp. Table 3 includes properties for the prepared tablets.

TABLE 3

Selected properties of tablet for oral suspension

| Tablet Property | Result |
|---|---|
| Target Tablet Weight | 487 mg |
| Individual Tablet Weight Range: | 487 mg ± 5% (462.7 mg-511.3 mg) |
| Average Tablet weight range: | 487 mg ± 2% (477.3 mg-496.7 mg) |
| Target Tablet Hardness: | 10.0 kp |
| Individual Tablet Hardness Range: | 6.0 kp-14.0 kp |
| Target Tablet Thickness: | 4.80 mm |
| Individual Tablet Range of Thickness: | 4.40 mm-5.20 mm |
| Loss on Drying | NMT 3.0% |
| Friability: | NMT 1.0% |
| Disintegration time | NMT 3 min at 25 ± 2° C. |
| Dissolution time | NLT 80% (Q) of the CGA labeled amount dissolved in 15-min. |

A long-term (25° C. 2° C. and 60% relative humidity, controlled room temperature (CRT)) stability study was conducted for representative tablets (e.g., Batch 3) while stored in a closed bottle that included 60 tablets and a silica gel cannister (2 g). Bottle details are as follows: 90 cc bottle (38 mm white HDPE EVOH round bottle) with a closure (38 mm CRC closure). Table 4 represents selected observables from the long-term stability study, where observables were evaluated according to USP. See USP 35 General Chapters <731> and <621>; see also Mattei at paras. 146-147.

TABLE 4

Stability study results

| Test | Spec. | Initial | 3M | 6M[a] | 9M | 12M | 18M | 24M |
|---|---|---|---|---|---|---|---|---|
| Loss on Drying | NMT 3.0% | 1.00 | 0.99 | 1.51 | 0.97 | 0.84 | 1.27 | 2.01 |
| CGA Assay | 95.0-105.0% | 100.3 | 100.3 | 96.8 | 100.0 | 100.7 | 100.8 | 100.4 |
| Imp. 1[b] | NMT 0.15% | 0.004 | 0.004 | 0.002 | 0.001 | 0.001 | 0.004 | 0.002 |
| Imp. 2[c] | NMT 0.15% | 0.051 | 0.042 | 0.042 | 0.028 | 0.045 | 0.043 | 0.035 |
| Imp. 3[d] | NMT 0.15% | 0.016 | 0.011 | 0.012 | 0.006 | 0.012 | 0.009 | 0.006 |
| Total Imps. | NMT 0.5% | 0.07 | 0.06 | 0.07 | 0.03 | 0.06 | 0.09 | 0.11 |

Notes:
[a]6M analyses conducted at 180-days.
[b]Imp. 1 corresponds to 2-oxo-pyrrolidone-(5S)-carboxylic acid.
[c]Imp. 2 corresponds to (4S)-2,5-dioxo-4-imidazolidinepropanoic acid.
[d]Imp. 3 corresponds to the sum of two impurities (viz., hexahydro-2,7-dioxo-1H-1,3-diazepine-(4S)-carboxylic acid and 1-carbamoyl-5-oxo-pyrrolidine-(2S)-carboxylic acid).

The stability study results show that manufactured tablets (e.g., Batch 3) exhibit long-term stability, where the carglumic acid shows no appreciable degradation after two years at CRT with compliant CGA assay results (e.g., 95.0-105.0%), as well as minuscule amounts of impurities, including Impurity 1, Impurity 2, Impurity 3, and total impurities. Additional studies (not included) show that manufactured tablets (e.g., Batch 3) have no appreciable degradation after three years at CRT with compliant CGA assay results and impurity levels.

In use stability results reveal that an opened bottle of manufactured tablets may be used for at least 90-days or more (e.g., 120-days). As stated above, Carbaglu® tablets must be discarded after one-month once the bottle has been opened. Thus, tablets for oral suspension, as disclosed herein, exhibit at least a three-fold improvement for in use stability when compared to Carbaglu® tablets.

For instance, representative tablet(s) for oral suspension (e.g., Batch 3) packaged in 60 count bottle (fifteen bottles total) were used for the study. One tablet was taken out from the bottle on every alternate day (except Sundays and holidays). The cap was placed again on the bottle without seal. The bottles were stored at room temperature (about 25° C. to about 30° C. (simulating real time patient use temperature condition)) throughout the study period. This sampling was continued for a period of 60 days. After this, the bottle was only opened and closed every day until 120 days (without sampling out any tablets). The remaining tablets were tested for description, loss on drying, disintegration, dissolution, CGA assay, organic impurities, and microbial test (results not shown). Table 5 presents selected results observed during the in-use stability.

TABLE 5

Selected results of in-use stability study

| Test | Initial | 120-days |
|---|---|---|
| CGA Assay | 100.3 | 100.0 |
| Imp. 1[a] | 0.004 | 0.004 |
| Imp. 2[b] | 0.051 | 0.042 |
| Total Imps. | 0.07 | 0.06 |
| Loss on drying | 1.00% | 1.35% |
| Disintegration | 22 sec | 24 sec |
| Dissolution (15 min) | 100% | 101% |

Notes:
[a]Imp. 1 corresponds to CAS No. 98-79-3.
[b]Imp. 2 corresponds to CAS No. 17027-50-8.

Based on these results, including others not reported herein, an opened bottle of manufactured tablets for oral suspension may be used for at least 90-days or more (e.g., 120-days).

Dissolution data were evaluate using USP Apparatus 2 (Paddle), 100 rpm, in 750 mL of an aqueous medium, e.g., 0.1 N HCl (pH 1.0), acetate buffer (pH 4.5), phosphate buffer (pH 6.8), and water. Table 6 reports the dissolution profile results for tablets (e.g., Batch 3) in aqueous media.

TABLE 6

Dissolution profile results in aqueous media

| Medium | Interval (min) | | | | |
|---|---|---|---|---|---|
| | 5 | 10 | 15 | 20 | 30 |
| 0.1N HCl (pH 1.0) | 98 | 100 | 100 | 100 | 100 |
| Acetate Buffer (pH 4.5) | 96.3 | 99 | 99 | 99 | 98 |
| 0.05M Phosphate Buffer (pH 6.8) | 100 | 101 | 100 | 101 | 101 |
| Water | 95 | 98 | 99 | 99 | 99 |

Tablets for oral suspension disclosed herein may be scored to obtain various dosage amounts. As a part of the development work, studies were conducted to investigate the mass loss observed after tablet splitting, along with friability.

For instance, a mass loss study for a representative batch (e.g., Batch 3) determined the weights of 15 tablets (A) and the weights of the split tablets (B, C, D, and E), where tablets were split either manually (by hand) or mechanically (using a tablet splitter). The total weight was calculated for each of the split tablets (F), which provided the basis for a loss of mass determination (viz., percent loss of mass=100×(A-F)/A). Table 7 presents the averages, minimum, and maximum values observed for the mass loss study for manually and mechanically split tablets.

TABLE 7

Mass loss study

| Observable | (mg) | | | | | | Loss of Mass (%) |
|---|---|---|---|---|---|---|---|
| | A | B | C | D | E | F | |
| Manually Split Tablets (N = 15) | | | | | | | |
| Avg. | 483.81 | 127.47 | 116.33 | 113.79 | 123.08 | 480.67 | 0.65 |
| Min. | 477.8 | 115.3 | 106.6 | 101.0 | 114.9 | 468.7 | 0.04 |
| Max. | 490.3 | 141.0 | 129.1 | 123.6 | 132.6 | 488.3 | 1.94 |
| Mechanically Split Tablets (N = 15) | | | | | | | |
| Avg. | 486.53 | 124.81 | 115.99 | 120.05 | 123.23 | 484.09 | 0.50 |
| Min. | 478.5 | 106.7 | 105.3 | 110.2 | 114.4 | 465.5 | 0.00 |
| Max. | 495.1 | 135.0 | 125.5 | 132.2 | 133.8 | 488.8 | 2.72 |

The Table 7 results from the mass loss study show that tablets for oral suspension having a hardness of about 10 kp are within the 3% limit for the individual segments.

As split tablets may be returned to the bottle, it was of interest to investigate the extent with which the split tablets tend to chip, crumble, or break which is reflected in the percent friability. Split tablets from a representative batch (e.g., Batch 3) having a total weight of about 6.5 g were investigated according to USP <1216>, Tablet Friability. Table 8 shows the results of the friability study.

TABLE 8

Friability study of split tablets

| Sample | Initial Wt. (A), g | Final Wt. after 100 Revolutions (B), g | % Friability = 100 × (A − B)/A |
|---|---|---|---|
| Manually Split Tablets | | | |
| Split Tablet 1 | 6.5674 | 6.5505 | 0.26 |
| Split Tablet 2 | 6.5537 | 6.5241 | 0.45 |
| Split Tablet 3 | 6.5634 | 6.5354 | 0.43 |
| Split Tablet 4 | 6.5202 | 6.5059 | 0.22 |
| Mechanically Split Tablets | | | |
| Split Tablet 1 | 6.5882 | 6.5378 | 0.77 |
| Split Tablet 2 | 6.5734 | 6.5295 | 0.67 |
| Split Tablet 3 | 6.5964 | 6.5586 | 0.57 |
| Split Tablet 4 | 6.5970 | 6.5586 | 0.31 |

The results from Table 7 shows that a tablet for oral suspension, as disclosed herein, exhibits a % friability of NMT 1%, which assures a low impact on patient safety and product efficacy.

Additional studies (not shown) reveal that split tablets for oral suspension, as disclosed herein, showed suitable content uniformity and stability for the in-use period of 90-days or more (e.g., 120-days).

Bioequivalence Study

A bioequivalence study was conducted to compare and evaluate the oral bioavailability of a tablet for oral suspension, as disclosed herein, e.g., Batches 1-3, with that of Carbaglu® (carglumic acid) tablets 200 mg in healthy, adult, human subjects under fasting conditions.

This open label, randomized, two-period, two-treatment, two-sequence, crossover, balanced, single dose oral bioequivalence study in healthy, adult, human subjects (18 to 45 years old) under fasting conditions was conducted to compare and evaluate the oral bioavailability of Test Product (viz., a tablet for oral suspension, as disclosed herein, e.g., Batches 1-3) with that of the Reference Product (viz., Carbaglu® (carglumic acid) tablets 200 mg). The study was conducted with 24 (20 completed) subjects in accordance with the protocol. After an overnight fasting of at least 10 hours, A single dose (100 mg/kg) of either Test Product or Reference Product was administered to the subjects as per a randomization schedule in a sitting posture with about 250 mL of water at ambient temperature under the supervision of trained study personnel as per the protocol. The interval between doses was 10 days.

Protocol: The Investigative Product (e.g., Test Product or Reference Product) was supplied as 200 mg tablets, the dose for each subject was calculated by multiplying the subject's weight by 100 mg/kg and then rounding up to the next 200 mg dose. The demographic details for dosed subjects (N=24) are: age (32±7 yrs), weight (64.3±11.5 kg), height (167.2±6.0 cm), and BMI (23.0±3.7 kg/m$^2$), while the demographic details for completed subjects (N=20) are: age (33±7 yrs), weight (64.3±12.2 kg), height (166.8±6.2 cm), and BMI (23.0±3.9 kg/m$^2$). The Investigative Product was dispersed (using stainless steel spatula) in 150 mL of purified water in a glass, immediately before administration to make a liquid dispersion without any lumps. The Investigative Product did not dissolve completely in water and un-dissolved particles of the Investigative Product may remain in the glass. Administer (to drink) the liquid dispersion of fully dispersed tablets to the subject. The glass used for dispersion of tablet was rinsed with additional 100 mL of water and was given to subject to ensure 250 mL of water was administered. This activity was followed by mouth check of the subjects to assess compliance to dosing. Note: Investigational products (Test or Reference) were not swallowed whole or crushed and dose was calculated considering the weight measured at the time of check-in (day-1) of each period.

Blood samples were collected at pre-dose (0.0 hours) and at intervals (e.g., Pre-dose (0.0 hour) and at 0.25, 0.5, 1.0, 1.5, 2.0, 2.333, 2.667, 3.0, 3.333, 3.667, 4.0, 5.0, 6.0, 8.0, 12.0, 16.0, 24.0, 36.0 and 48.0 hours post dose in each period) over 48.0 hours after administration of each dose. The plasma samples were shipped to an analytical facility for analysis. Statistical analysis was performed by a third-party to compare and evaluate the oral bioavailability of the Test Product to the Reference Product.

The order of receiving of the Investigational Products for each subject was determined according to a randomization schedule. Subjects were randomized to one of the two sequences: either Test Product/Reference Product (TR) or Reference Product/Test Product (RT). Dosing was followed by a washout period of 10-days.

In total, 20 subjects were completed both the periods of the study and their data were considered for PK analysis and out of 20 subjects.

Table 9 (Test Product) and Table 10 (Reference Product) include observed and calculated (Phoenix® WinNonlin® software version 8.0) PK parameters for a tablet for oral suspension, as disclosed herein, e.g., Batches 1-3 (or Test Product), and Carbaglu® (tablets, 200 mg, Reference Product).

Observed and calculated PK parameters include Mean, SD, Geometric mean, CV %, ISCV %, Range (Minimum and Maximum), and Median for $C_{max}$, $AUC_{0-t}$ (calculated using the linear trapezoidal rule from the zero time point to the last quantifiable concentration), $AUC_{0-\infty}$, $T_{max}$, $T_{1/2}$ (calculated from the expression $T_{1/2}$=0.693/Kel), Kel, and AUC_% Extrap_obs (percentage of extrapolated AUC or "AUC % EO," the residual area in percentage determined according to the following [(AUCi−AUCt)/AUCi]×100, where AUCi is the area under the plasma carglumic acid concentration versus time curve from zero to infinity calculated by adding Ct/Kel to AUCt, where Ct is the last quantifiable concentration and Kel is the elimination rate constant).

TABLE 9

PK Parameters for Carglumic Acid (Test Product), N = 20

|  | $C_{max}$ (ng/mL) | $AUC_{0-t}$ (hr*ng/mL) | $AUC_{0-\infty}$ (hr*ng/mL) | $T_{max}$ (hr) | $T_{1/2}$ (hr) | Kel (1/hr) | AUC % EO |
|---|---|---|---|---|---|---|---|
| Mean | 3880.7653 | 33544.6546 | 36521.3851 | 2.730 | 15.570 | 0.0722 | 7.70 |
| SD | 1412.57648 | 11606.43693 | 13219.26515 | 1.045 | 10.018 | 0.0501 | 5.57 |
| CV % | 36.40 | 34.60 | 36.20 | 38.23 | 64.32 | 69.43 | 72.34 |
| Median | 3478.973 | 31259.964 | 34586.390 | 2.33 | 14.8 | 0.0511 | 6.52 |
| Min | 1576.163 | 16199.898 | 17428.445 | 1.00 | 3.92 | 0.0208 | 1.95 |
| Max | 7585.521 | 62752.545 | 67854.578 | 5.00 | 33.24 | 0.1769 | 22.60 |

TABLE 10

PK Parameters for Carglumic Acid (Reference Product), N = 20

|  | $C_{max}$ (ng/mL) | $AUC_{0-t}$ (hr*ng/mL) | $AUC_{0-\infty}$ (hr*ng/mL) | $T_{max}$ (hr) | $T_{1/2}$ (hr) | Kel (1/hr) | AUC % EO |
|---|---|---|---|---|---|---|---|
| Mean | 5643.4812 | 37606.4796 | 41488.2903 | 2.27 | 20.39 | 0.046 | 9.75 |
| SD | 4744.90267 | 13507.30938 | 14088.79117 | 1.34 | 10.017 | 0.03027 | 7.01 |
| CV % | 84.08 | 35.92 | 33.96 | 58.80 | 49.13 | 65.75 | 71.85 |
| Median | 4592.942 | 36517.758 | 38138.996 | 2.33 | 21.38 | 0.0327 | 7.85 |
| Min | 1572.218 | 18900.279 | 25662.217 | 0.25 | 5.36 | 0.0147 | 1.82 |
| Max | 23665.322 | 81589.390 | 88190.805 | 6.00 | 47.01 | 0.1294 | 33.19 |

The Bioequivalence was concluded based on the 90% confidence interval of geometric least square mean ratio of $C_{max}$, $AUC_{0-t}$ and $AUC_{0-\infty}$ (carglumic acid) of the Test Product and Reference Product were within 80.00% to 125.00% for ln-transformed data. See Table 11 below.

TABLE 11

Test & Reference Geometric mean, Ratio, ISCV, 90% Confidence Intervals, Acceptance Criteria and Outcome of BE result based on Ln-transformed data for Carglumic acid (N = 18)

| Parameters | Geometric Mean† | | Ratio (%) | ISCV (%) |
|---|---|---|---|---|
|  | Test | Reference | | |
| $C_{max}$ (ng/mL) | 3530.0478 | 4001.6539 | 88.21 | 14.24 |
| $AUC_{0-t}$ (hr*ng/mL) | 31573.164 | 34615.966 | 91.21 | 15.13 |
| $AUC_{0-\infty}$ (hr*ng/mL) | 34526.489 | 38908.986 | 88.74 | 15.21 |

| Parameters | 90% Confidence Intervals | Acceptance Criteria | Outcome of BE result |
|---|---|---|---|
| $C_{max}$ (ng/mL) | 80.83%-96.28% | 80%-125% | Bioequivalent |
| $AUC_{0-t}$ (hr*ng/mL) | 83.12%-100.09% | 80%-125% |  |
| $AUC_{0-\infty}$ (hr*ng/mL) | 80.83%-97.42% | 80%-125% |  |

†Two subjects were excluded from the BE analysis based on statistical considerations.

The Table 11 results reveal that a tablet for oral suspension, as disclosed herein, e.g., Batches 1-3, exhibit bioequivalence with respect to Carbaglu®. According to current regulatory guidance, bioequivalence can be declared when each of the 90% confidence interval (CI) for the ratio of mean values for the maximum carglumic acid blood concentration ($C_{max}$) and the carglumic acid blood area-under-the curve (AUC) for the tablet for oral suspension and Carbaglu® falls within the interval 80-125%, as evaluated in a randomized, cross-over trial. Indeed, the tablet for oral suspension disclosed herein is the subject of ANDA 213729, which was approved by the FDA on Oct. 13, 2021.

Nasogastric Studies

The FDA's Draft Guidance on Carglumic Acid recommends studies to conduct for establishing bioequivalence. As tablets for oral suspension may be administered by a tube (nasogastric or gastric), the FDA recommends conducting in vitro feeding tube studies including comparative recovery testing and sedimentation volume testing.

Comparative in vitro feeding tube studies were performed with respect to tablets for oral suspension (e.g., Batch 3) and Carbaglu® tablets.

Specifically, comparative recovery studies were conducted to determine the percentage of the initial dose that passes through a combination of oral syringe and feeding tubes, including: (i) polyurethane (5 French ("Fr."), 1.7 mm inner diameter (ID), length (L) of 91 cm); (ii) polyurethane (8 Fr., 2.7 mm ID, L of 107 cm); (iii) polyvinyl chloride (5 Fr., 1.7 mm ID, L of 91 cm); (iv) polyvinyl chloride (8 Fr., 1.7 mm ID, L of 90 cm); (v) silicone (5 Fr., 1.7 mm ID, L of 90 cm); and (vi) silicone (8 Fr., 2.7 mm ID, L of 90 cm). The oral syringes (12 no.) had a volume of 3 mL with a polypropylene barrel and a plunger comprised of white high-density polyethylene.

A suspension was prepared by mixing a 200 mg tablet in a minimum of 2.5 mL with gentle shaking to allow for dispersal. The suspension was drawn into the syringe where the suspension was passed through the syringe and the feeding tube into a collection container. The tube (e.g., NG tube) was flushed with 2 mL water. The percentage of carglumic acid recovered was determined at the tube exit relative to the initial dose for both the tablet(s) for oral suspension and the Carbaglu® tablet(s) using a validated analytical method.

Except for the silicone (5 Fr.) tube, all tubes were satisfactory for the table for oral suspension and Carbaglu®. Table 12 summarizes the NG feeding tube studies for tablet(s) for oral suspension ("T") and Carbaglu® tablets ("R").

TABLE 12

Summary of NG feeding tube studies

| Tubing type (size) | Mean Ratio (T/R) | 90% CI Lower | 90% CI Upper |
|---|---|---|---|
| Polyurethane (5 Fr.) | 0.984 | 95.13 | 101.83 |
| Polyurethane (8 Fr.) | 1.047 | 102.91 | 106.52 |
| PVC (5 Fr.) | 1.019 | 98.55 | 105.31 |
| PVC (8 Fr.) | 0.993 | 97.85 | 100.93 |
| Silicon (8 Fr.) | 1.015 | 100.02 | 103.05 |

The results for the 90% confidence interval ("CI") were in the range of 95.13% to 106.52% demonstrating similar performance of the tablet(s) for oral suspension compared to Carbaglu® tablets in the different types of nasogastric tubes evaluated.

Comparative recovery studies were conducted to determine the percentage of the initial dose that passes through a combination of oral syringe and feeding tube. The study was conducted immediately (i.e., 0 min). Repeated the study after waiting (soaking time) for 15 minutes. The suspension was taken into the syringe and attached to feeding tube and the dispersion passed through the feeding tube into a collection container. Flushed the NG tube with 2 mL water. Determined the percentage of Carglumic Acid recovered at the tube exit relative to the initial dose for both the tablet for oral suspension ("Test" or "T") and Cabaglu® tablet ("Reference" or "R") products using a validated analytical method. Additional pressure needed to be applied during the testing to ensure complete recovery was documented as observations.

For particle size measurements, the syringe was attached to the feeding tube. Then, using the syringe plunger, the suspension was pushed through the syringe and the feeding tube into a collection container. The particle size distribution of the collected fluid was measured using Malvern Mastersizer 2000 particle size analyzer using water as dispersant (refractive index (1.33) and absorption (0.1)) with a measurement time of 12-sec, and a background time of 12-sec. Samples were added dropwise using a transfer pipette until obscuration of 10%-20% is achieved, operating at 2400 rpm and employing three measurement cycles. Table 13 reports the Dv(10), Dv(50), and Dv(90) (or D10, D50, D90) values (in μm), as well as the percent coefficient of variation (% CV) and the D-span, which reflects the breadth of the volume-based distribution between the D10 and D90-values, normalized to the D50-value (i.e., D-span=(D90-D10)/D50).

values. Additionally, the 15-min soaking data shows that the Carbaglu® product may exhibit particle aggregation as seen from the D10-, D50-, and D90-values-cf, R D90-value of 92.1 μm (0-min) vs. R D90-value of 232.3μ (15-min). As the tablets for oral suspension do not exhibit particle aggregation after a 15-min soaking suggests that the suspending agent (e.g., povidone having a weight average molecular weight of from 44 kDa to 54 kDa) effectively suspends the CGA particles present in the suspension, which suggests reduced variability with absorption (viz., Cmax- and AUC-values).

Practical Utility and Advantages

The tablet for oral suspension disclosed herein is the subject of ANDA 213729 and has been established to be bioequivalent with Carbaglu®.

The tablet for oral suspension disclosed herein exhibits improved long-term storage stability at 25° C.±2° C. and 60% relative humidity for at least 2-years or more (e.g., 3-years).

The tablet for oral suspension disclosed herein exhibits improved in-use stability for at least 90-days or more (e.g., 120-days).

The suspending agent (e.g., povidone having a weight average molecular weight of from 44 kDa to 54 kDa) effectively suspends the CGA particles present in the suspension, which suggests reduced variability with absorption (viz., Cmax- and AUC-values).

Definitions and Abbreviation

Definitions of some of the terms used herein to describe the invention are detailed below.

The use of the terms "a" and "an" and "the" and similar references in the context of describing the tablet disclosed herein (especially in the context of the following claims) are to be construed to cover both the singular and the plural, unless otherwise indicated herein or clearly contradicted by context.

The term "about" is as used herein embodies standard error associated with a physicochemical observable to reflect the reality of experimental uncertainty associated with a given measurement for the physicochemical observable. As used herein, the term "about" means a slight variation of the value specified, for example, within 10% of the value specified. USP 35, Sect. 8.20. A stated amount for a compositional ingredient that is not preceded by the term

TABLE 13

Particle size distribution data for Test and Reference product suspension

| Product | Observable | Initial | | | 0 min | | | 15 min | | |
|---|---|---|---|---|---|---|---|---|---|---|
| | | D10 (μm) | D50 (μm) | D90 (μm) | D10 (μm) | D50 (μm) | D90 (μm) | D10 (μm) | D50 (μm) | D90 (μm) |
| T | Mean | 23.1 | 72.1 | 149.2 | 21.7 | 69.9 | 145.1 | 21.1 | 67.4 | 142.8 |
| | % CV | 10 | 4 | 3 | 12 | 4 | 2 | 14 | 8 | 6 |
| | D-span[a] | | 1.75 | | | 1.76 | | | 1.81 | |
| R | Mean | 6.0 | 34.6 | 92.3 | 6.0 | 34.6 | 92.1 | 27.3 | 96.9 | 232.3 |
| | % CV | 2 | 1 | 1 | 1 | 1 | 1 | 11.4 | 7.7 | 6.8 |
| | D-span[a] | | 2.42 | | | 2.46 | | | 2.12 | |

[a]D-span = (D90 − D10)/D50.

Based on these results, one may see that the tablets for oral suspension (T) exhibit uniformity of D-values and D-span regardless of the extent of soaking. This contrasts with the Carbaglu® tablets (R), which exhibit larger D-span "about" does not mean that there is no variance for the stated term, as one would understand that there may be the possibility of a degree of variability generally associated with experimental error.

The term "therapeutically effective amount" or "effective dose" as used herein refers to the amount or dose of carglumic acid that is sufficient to initiate a therapeutic response in a patient.

Abbreviated terms used herein include: µm (micrometer), Abbreviated New Drug Application (ANDA), average (Avg.), plasma carglumic acid concentration area under the curve (AUC), area under the plasma carglumic acid concentration versus time curve from the zero time point to the last quantifiable concentration ($AUC_{0-t}$), area under the plasma carglumic acid concentration versus time curve from the zero time point to infinity ($AUC_{0-\infty}$), bioequivalence (BE), carbamoyl-phosphate synthase (CPS), carglumic acid (CGA), Chemical Abstract Service (CAS), child resistant cap (CRC), colloidal (Coll.), coefficient of variation (CV %), confidence interval (CI), controlled room temperature (CRT), Daltons (Da) (g/mol), elimination rate constant (Kel), estimated glomerular filtration (eGFR), ethylene-vinyl alcohol copolymer (EVOH), gastrostomy (G), high density polyethylene (HDPE), inverse of sample coefficient of variation (ISCV %), kilogram (kg), kilopond (kp), magnesium stearate (MS), maximum carglumic acid plasma concentration (Cmax), microcrystalline cellulose (MCC), milligram (mg), milliliter (mL), N-acetyl-glutamate synthase (NAGS), nasogastric (NG), not less than (NLT), not more than (NMT), particle size (PS), particle size distribution (PSD), pharmacokinetic (PK), Reference Product (R), sodium lauryl stearate (SLS), sodium stearyl fumarate (SSF), standard deviation (SD), Test Product (T), time of the maximum measured carglumic acid plasma concentration ($T_{max}$), U.S. Food and Drug Administration (FDA), United States Pharmacopeia (USP), weight (Wt.), and weight average molecular weight (Mw).

CITED INFORMATION

The following cited information is incorporated by reference in its entirety. If incorporated subject matter conflicts with the meaning of subject matter disclosed herein, the subject matter disclosed herein controls.

ASTM E-11-20, available online at newarkwire.com/pdf/ASTM %20E11-20.pdf, last accessed on Apr. 14, 2022 ("ASTM E-11").
Carbaglu® Prescribing Information, as of Aug. 5, 2021.
CAS Registry No. 1188-38-1, carglumic acid (2022).
CAS Registry No. 98-79-3, Impurity 1 (2022).
CAS Registry No. 17027-50-8, Impurity 2 (2022).
CAS Registry No. 2380660-24-0 (2022).
Chinese Published Application No CN 105056246 A, Carglumic acid solid composition and preparation method thereof, published on Nov. 18, 2015 to Xingfa et al. of Wuhan Wuyao Technology ("Xingfa").
European Medicines Agency Scientific Discussion related to Carbaglu® (2004).
European Patent Specification No. EP 2 777 696 B1, Preparation of stable pharmaceutical dosage forms, published on Apr. 21, 2021 to Kawale et al. of Navinta, LLC ("Kawale").
International Publication No. WO 2018/095848 A1, Pharmaceutical parenteral formulation containing carglumic acid, published on May 31, 2018 to Berlati et al. of Recordati Industria Chimica E Farmaceutica S.P.A. ("Berlati").
International Publication No. WO 2020/239882 A1, Pharmaceutical formulation for carglumic acid, published on Dec. 3, 2020 to Mattei et al. of Recordati Industria Chimica E Farmaceutica S.P.A. ("Mattei").
Primellose® (croscarmellose sodium) safety information (2020).
Product Bulletin for Stepanol® WA-100 NF/USP (2015).
Product information for CAB-O-SIL® (2021).
Product Information for LIGAMED MF-2-K (2018).
Product Information for Pruv®, accessible at www.jrspharma.com/pharma-wAssets/docs/brochures/pruv-gb-1809.pdf, last accessed on Apr. 14, 2022.
Product Specifications for Avicel® PH-113 (2003).
Product Specifications for Pearlitol® 200 SD (2020).
Remington: *Practice of the science and pharmacy*, Vol. II, pp. 1598-1649 (1995).
Technical information for Kollidon® (2019).
The FDA's June 2020 Draft Guidance on Carglumic Acid, available at www.accessdata.fda.gov/drugsatfda_docs/psg/PSG_022562.pdf, last accessed on Apr. 14, 2022.
The FDA's Oct. 13, 2021 approval letter with respect to ANDA 213729 held by Novitum Pharma LLC.
The United States Pharmacopeia 35—National Formulary 30 (2012), pages 3-15, 258-265, 293-295, 317-318, 336-339, 343-344, 867-870, 5637-5640, 5642-5649 ("USP 35").

The invention claimed is:

1. A tablet for oral suspension, comprising:
   carglumic acid in an amount of about 200 mg;
   a diluent comprising microcrystalline cellulose, mannitol, or a combination thereof in an amount of from 228 mg to 280 mg;
   a suspending agent comprising a povidone having a weight average molecular weight of from 44 kDa to 54 kDa in an amount of from 4.4 mg to about 5.4 mg;
   a disintegrant comprising sodium croscarmellose in an amount of from 17 mg to 21 mg;
   a wetting agent comprising sodium stearyl fumarate, magnesium stearate, sodium lauryl sulfate, or a combination thereof in an amount of from 6.35 mg to 7.65 mg; and
   a glidant comprising colloidal silicon dioxide in an amount of from 2.3 mg to 2.8 mg;
   wherein the tablet does not include tromethamine or an effervescent agent.

2. The tablet of claim 1, wherein the diluent comprises microcrystalline cellulose in an amount of from 149 mg to 183 mg and mannitol in an amount of from 79 mg to 98 mg.

3. The tablet of claim 1, wherein the wetting agent comprises sodium stearyl fumarate in an amount of from 4.5 mg to 5.5 mg, magnesium stearate in an amount of from 1.4 mg to 1.6 mg, and sodium lauryl sulfate in an amount of from 0.45 mg to 0.55 mg.

4. The tablet of claim 1, wherein
   the diluent comprises microcrystalline cellulose, mannitol, or a combination thereof in an amount of from 240 mg to 266 mg;
   the suspending agent comprises povidone having a weight average molecular weight of from 44 kDa to 54 kDa in an amount of from 4.6 to 5.1 mg;
   the disintegrant comprises sodium croscarmellose in an amount of from 18 mg to 20 mg;
   the wetting agent comprises sodium stearyl fumarate, magnesium stearate, sodium lauryl sulfate, or a combination thereof in an amount of from 6.7 mg to 7.4 mg; and
   the glidant comprises colloidal silicon dioxide in an amount of from 2.4 mg to 2.6 mg.

5. The tablet of claim 4, wherein the diluent comprises microcrystalline cellulose in an amount of from 158 mg to 174 mg and mannitol in an amount of from 82 mg to 92 mg.

6. The tablet of claim 4, wherein the wetting agent comprises sodium stearyl fumarate in an amount of from 4.8 mg to 5.3 mg, magnesium stearate in an amount of from 1.4 mg to 1.6 mg, and sodium lauryl sulfate in an amount of 0.5 mg.

7. The tablet of claim 1, wherein
the diluent comprises microcrystalline cellulose, mannitol, or a combination thereof in an amount of from 249 mg to 258 mg;
the suspending agent comprises povidone having a weight average molecular weight of from 44 kDa to 54 kDa in an amount of from 4.8 to 5.0 mg;
the disintegrant comprises sodium croscarmellose in an amount of from 18.6 mg to 19.4 mg;
the wetting agent comprises sodium stearyl fumarate, magnesium stearate, sodium lauryl sulfate, or a combination thereof in an amount of from 6.87 mg to 7.13 mg; and
the glidant comprises colloidal silicon dioxide in an amount of from 2.45 mg to 2.55 mg.

8. The tablet of claim 7, wherein the diluent comprises microcrystalline cellulose in an amount of from 163 mg to 169 mg and mannitol in an amount of from 86 mg to 89 mg.

9. The tablet of claim 7, wherein the wetting agent comprises sodium stearyl fumarate in an amount of from 4.9 mg to 5.1 mg, magnesium stearate in an amount of from 1.47 mg to 1.53 mg, and sodium lauryl sulfate in an amount 0.5 mg.

10. The tablet of claim 1, wherein
the diluent comprises microcrystalline cellulose, mannitol, or a combination thereof in an amount of 253.6 mg;
the suspending agent comprises povidone having a weight average molecular weight of from 44 kDa to 54 kDa in an amount of 1.01 mg;
the disintegrant comprises sodium croscarmellose in an amount of 19.0 mg;
the wetting agent comprising sodium stearyl fumarate, magnesium stearate, sodium lauryl sulfate, or a combination thereof in an amount of 7 mg; and
the glidant comprises colloidal silicon dioxide in an amount of 2.5 mg.

11. The tablet of claim 10, wherein the diluent comprises microcrystalline cellulose in an amount of 166 mg and mannitol in an amount of from 87.6 mg.

12. The tablet of claim 10, wherein the wetting agent comprises sodium stearyl fumarate in an amount of 5.0 mg, magnesium stearate in an amount of 1.5 mg, and sodium lauryl sulfate in an amount of 0.5 mg.

13. The tablet of claim 1, wherein the tablet comprises three equidistant lines for splitting the tablet into four equal portions each portion having a mass of about 122 mg.

14. A capped bottle comprising one or more tablets of claim 1 and a desiccant, wherein the tablet has a carglumic acid content of from 95.0% to 105% for two-years when the bottle is stored at 25° C.±2° C. and 60% relative humidity.

15. The bottle of claim 14, wherein the one or more tablets exhibits an in-use stability for 90-days when stored at a temperature of from about 25° C. to about 30° C.

16. An oral suspension comprising the at least one part of the tablet of claim 1 and about 2.5 mL of water.

17. The oral suspension of claim 16 having a D(0.9) particle size of about 146 µm.

18. A method of treating acute hyperammonaemia, which comprises administering to a patient in need thereof a therapeutically effective amount of the oral suspension of claim 16.

19. A method of treating chronic hyperammonaemia, which comprises administering to a patient in need thereof a therapeutically effective amount of the oral suspension of claim.

* * * * *